United States Patent [19]

Gao

[11] Patent Number: 5,314,469

[45] Date of Patent: May 24, 1994

[54] ARTIFICIAL HEART

[75] Inventor: Hua Gao, Shorewood, Wis.

[73] Assignee: Milwaukee Heart Research Foundation, Milwaukee, Wis.

[21] Appl. No.: 849,190

[22] Filed: Mar. 11, 1992

[51] Int. Cl.⁵ .................... A61M 1/10; A61N 1/362
[52] U.S. Cl. .......................................... 623/3; 600/16
[58] Field of Search ..................... 623/3; 600/16-18

[56] References Cited

U.S. PATENT DOCUMENTS

| | | |
|---|---|---|
| 3,046,903 | 7/1962 | Jones . |
| 3,152,340 | 10/1964 | Fry et al. . |
| 3,842,440 | 10/1974 | Karlson .................... 623/3 |
| 4,152,785 | 5/1979 | Shumakov et al. .......... 623/3 |
| 4,369,530 | 1/1983 | Robinson et al. ........... 623/3 |
| 4,468,177 | 8/1984 | Strimling ............... 623/3 X |
| 4,512,726 | 4/1985 | Strimling . |
| 4,524,466 | 6/1985 | Hall et al. ................ 623/3 |
| 4,623,350 | 11/1986 | Lapeyre et al. . |
| 4,718,903 | 1/1988 | Min et al. ................. 623/3 |
| 4,750,903 | 6/1988 | Cheng ...................... 623/3 |
| 4,820,300 | 4/1989 | Pierce et al. .............. 623/3 |
| 4,851,002 | 7/1989 | Slonina .................... 623/3 |
| 5,006,104 | 4/1991 | Smith et al. ............ 623/3 X |
| 5,064,353 | 11/1991 | Tsukahara .............. 623/3 X |
| 5,066,300 | 11/1991 | Isaacson et al. .......... 623/3 |
| 5,089,018 | 2/1992 | Lapeyre et al. ............ 623/3 |

OTHER PUBLICATIONS

An Electric Artificial Heart for Clinical Use, Annals of Surgery, Sep. 1990, pp. 339-343.
In Vivo Performance of a Transcutaneous Energy Transmission System . . . , Weiss et al., pp. 284-288.
Endothelialization of Vascular Prosthetic Surfaces After Seeding . . . , Rupnick et al., Journ. of Vascular Surgery.

Primary Examiner—Randall L. Green
Assistant Examiner—Elizabeth M. Burke
Attorney, Agent, or Firm—Foley & Lardner

[57] ABSTRACT

A cyclic action, electromechanically operated artificial heart having a pusher plate assembly disposed between a pair of bladders for alternately compressing one bladder containing blood directed to the pulmonary system and another bladder containing blood directed to the systemic circulatory system includes a mechanical linkage for translating unidirectional rotary motion of a motor located opposite of both bladders into reciprocating movement of the pusher plate assembly.

22 Claims, 6 Drawing Sheets

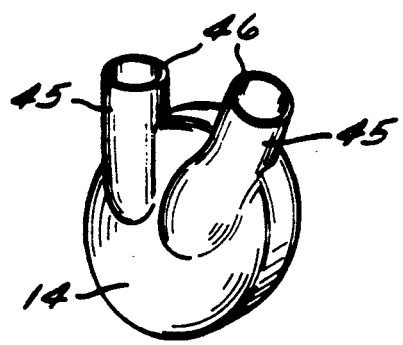
FIG. 5
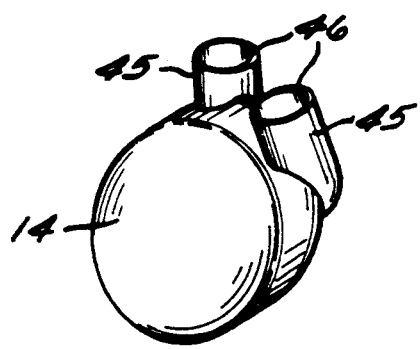
FIG. 6
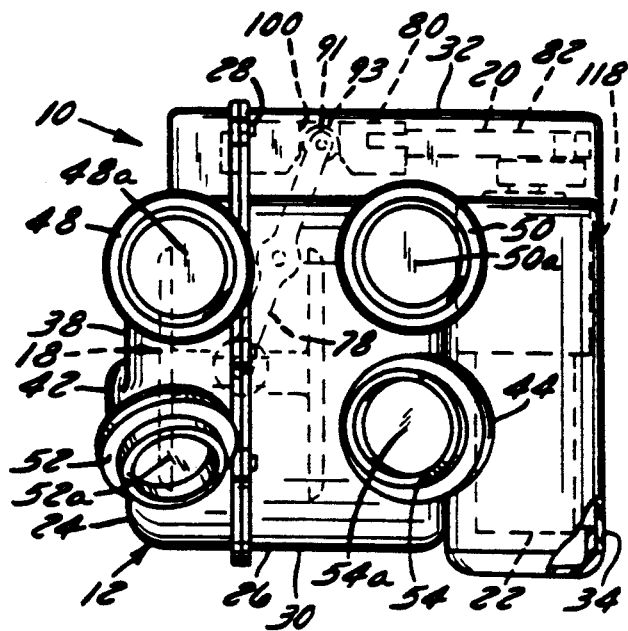
FIG. 2
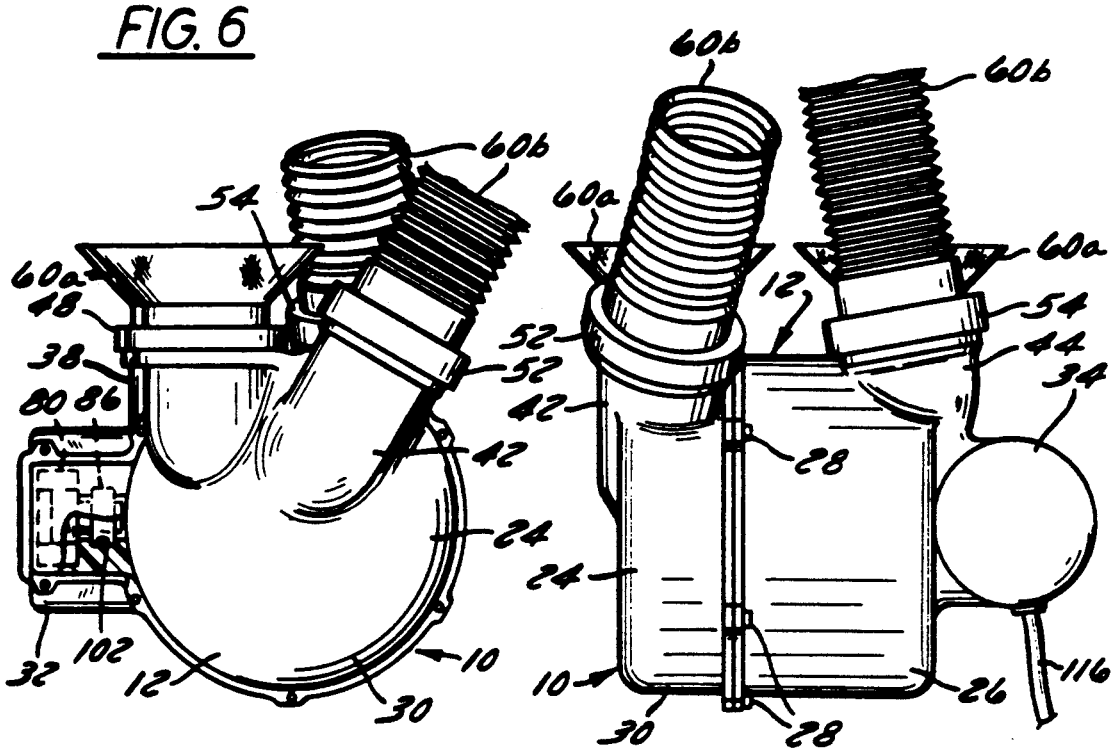
FIG. 4
FIG. 3

ARTIFICIAL HEART

FIELD OF THE INVENTION

This invention relates to an artificial heart, more particularly to an electromechanical artificial heart having improved flow dynamics to minimize trauma and clotting in the blood of a living recipient.

BACKGROUND OF THE INVENTION

Numerous artificial hearts and blood pumps have been devised to replace a defective or diseased heart and closely simulate the functioning of a healthy, natural heart. In contrast to heart transplantation, which requires a donor and involves serious rejection problems, a total artificial heart may be mass-produced and is potentially more compatible with the host's immune system. However, an artificial heart must be compact enough to fit in the chest cavity, and must consistently maintain proper blood flow based on the host's level of activity. The input and output flow characteristics of the artificial heart must be sufficient to protect the blood cells from hemolysis (dissolution) and thrombosis (clotting). The artificial heart mechanism must also be extremely reliable and durable.

One example of an artificial heart is disclosed in U.S. Pat. No. 3,152,340 issued Oct. 13, 1964 to Fry, et al. In this device, a piston and plate assembly is positioned between two diaphragms, or imitation heart chambers. A motor mounted above the chambers delivers a driving force to the piston and plate assembly and, in turn, to the diaphragms through an eccentric looped pitman for alternatively exhausting the chambers via back-and-forth movement of the piston and plate assembly. Flow into and out of the inlets and outlets is regulated by a set of floating plate valves located outside the inlets and outlets on respective valve boxes located laterally of the diaphragms.

U.S. Pat. No. 4,512,276 issued Apr. 23, 1985 to Strimling discloses another artificial heart having three pump chambers separated by a pair of diaphragms in contact with cooperating cam-equipped pusher plates. A variable length rod connects the pusher plates and holds a rotary electric motor carrying rollers which move the pusher plates by actuating the cams provided on each of the pusher plates to alternatively contact the diaphragms and effectuate pumping.

U.S. Pat. No. 4,820,300 issued Apr. 11, 1989 to Pierce, et al shows a further artificial heart which utilizes a fluid displaced from a left blood pump to power a right blood pump. The left blood pump is a sac-type pump powered by an electric motor that, when contracting or expanding, displaces a volume of fluid in a chamber within the left pump housing. The fluid is displaced through a fluid line connecting the right blood pump, which is a pneumatically operated sac-type or rotary-type pump.

Another artificial heart described in "An Artificial Heart For Clinical Use", *Annals of Surgery*, Sept. 1990, pp. 339-343 employs a pusher plate assembly between a pair of bladders for alternatively compressing each bladder by reciprocal movement of the pusher plate assembly. In a first version, a cam-type electric motor positioned between the bladders provides the driving force to reciprocate the pusher plate assembly. In a second version, a roller screw-type electric motor disposed intermediate the bladders transmits back-and-forth motion to the pusher plate assembly.

These known arrangements are generally deficient in meeting one or more of the requisites discussed above, and a need remains for a compact, reliable artificial heart which enables proper circulation of blood in the body.

SUMMARY OF THE INVENTION

The invention provides an artificial heart which includes a housing having pairs of inlet and outlet ports provided with suitable one-way valves. A pair of bladders are disposed in the housing. Each bladder communicates with an associated inlet and outlet. A pusher plate assembly is positioned between the bladders for alternatively compressing each bladder by back-and-forth motion of the pusher plate assembly. A motor is mounted in the housing to the side of the bladders and pusher plate assembly. The motor is connected to a mechanical linkage which, in turn, is joined to the pusher plate assembly. The motor transmits driving force through the mechanical linkage to the pusher plate assembly to reciprocate the pusher plate assembly so that the first and second bladders alternately fill with and eject blood when the artificial heart is implanted in a host. In a preferred embodiment, the mechanical linkage comprises a lever arm having one end which is pivotally connected to the pusher plate assembly and a center portion which is pivotally mounted to the housing. The other end of the lever arm is movably seated in a roller-mounted carriage. The carriage is fastened by a connecting link joined to a rotary crank arm on the motor.

According to further aspects of the invention, the valves are unidirectional, tilting plate inlet and outlet valves disposed within integrated valve seats in the first and second inlet and outlet ports, respectively, to permit either intake or egress of blood to or from the bladders. The bladders themselves are preferably flaccid sacs that minimize blood clotting.

An artificial heart according to another aspect of the invention includes a housing having first and second inlet ports and first and second outlet ports, first and second compressible chambers such as bladders disposed in the housing, the first chamber communicating with the first inlet and outlet ports and the second chamber communicating with the second inlet and outlet ports, and a drive system for alternately compressing the chambers to fill and eject blood in a manner that resembles the action of a natural heart. The improvement resides in a system that varies the speed of compression and decompression of the chambers from a minimum (zero) that occurs when each bladder reaches maximum compression to a maximum that occurs approximately midway between associated minima.

BRIEF DESCRIPTION OF THE DRAWINGS

The invention will be described with reference to the appended drawings, wherein like numerals denote like elements, and:

FIG. 2 is an elevational view of the artificial heart of FIG. 1;

FIG. 3 is a front view of the artificial heart of FIG. 2;

FIG. 4 is a partially cut-away end view taken from the left hand side of FIG. 3;

FIG. 5 and 6 are perspective views of the bladders shown in the artificial heart of FIG. 1;

DETAILED DESCRIPTION OF PREFERRED EMBODIMENTS

Figure 1:
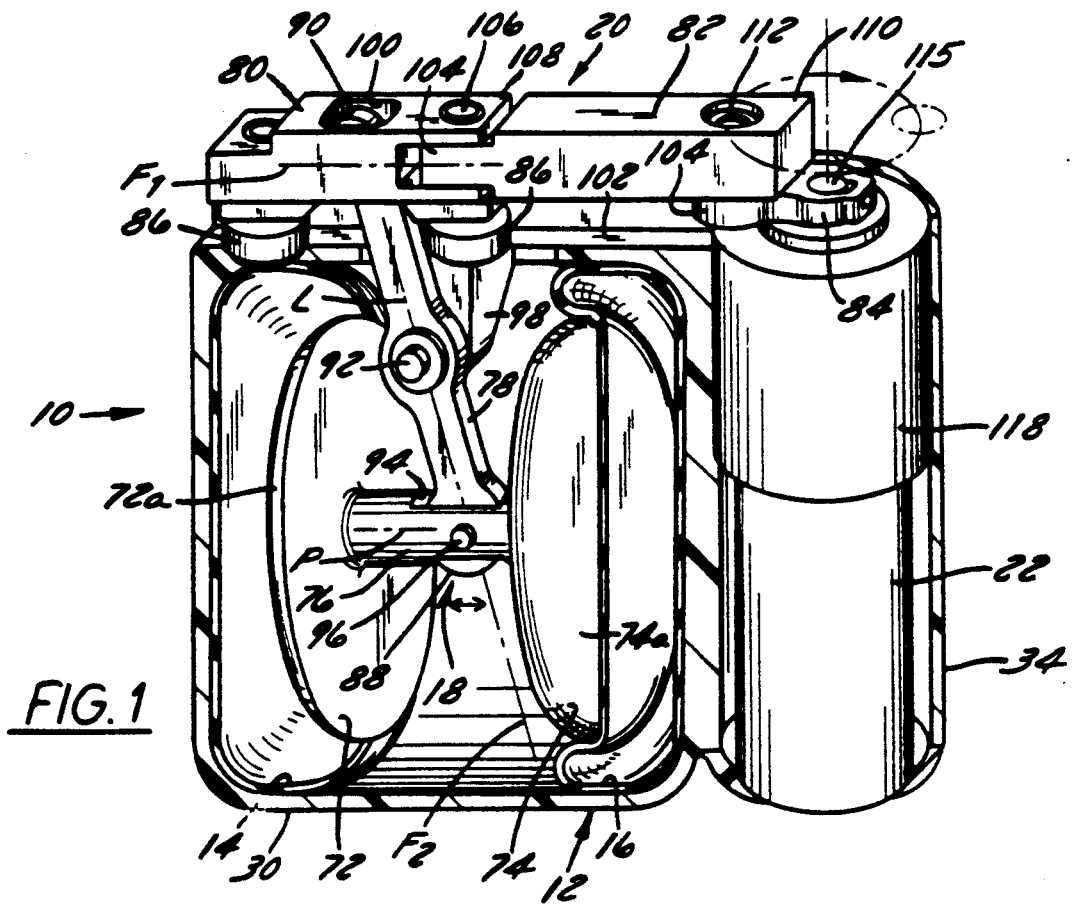
FIG. 1 is a perspective, cutaway view, partly in section, of an artificial heart according to the invention.

FIGS. 1 through 10 illustrate a representative artificial heart 10 in accordance with the invention which is adapted to be implanted in the chest cavity of a human host or certain other mammals to replace a defective natural heart and replicate the circulatory function of a natural heart. It should be appreciated from the following discussion that the invention contemplates a self-contained unit capable of extended operation using electromechanical energy instead of employing pneumatic or hydraulic power.

Referring first to FIGS. 1-4, artificial heart 10 generally comprises a housing 12, a pair of deformable bladders 14, 16, a reciprocating pusher plate assembly 18, a multi-piece mechanical linkage 20 and a DC motor 22. Housing 12 includes a pair of plastic, flanged mating sections 24, 26 sealingly joined together by fasteners 28 to form an enclosure 30 for bladders 14, 16 and pusher plate assembly 18 as well as a rear rectangular projection 32 that houses mechanical linkage 20. Mating section 26 includes an integral, generally cylindrical protective casing 34 for motor 22. Housing 12 is also formed with two inlet ports 38, 40 and two outlet ports 42, 44 in communication with the associated arteries and veins of the host.

Inlet port 38 and outlet port 42 communicate with bladder 14, while inlet port 40 and outlet port 44 communicate with bladder 16. Bladders 14, 16 serve as flaccid pumping sacs into which blood is received and from which blood is pumped out in a manner similar to the chambers of the natural heart. Bladders 14, 16 are preferably generally disc-shaped, with smooth inner and outer polyurethane walls having no crevices or corners in which blood could become stagnant and coagulate (see FIGS. 5 and 6.)

As best seen in FIGS. 5 and 6, each of bladders 14, 16 have a pair of spaced tubular extensions 45 ending in elastic mouths 46. Mouths 46 are fitted over the upper walls of a set of plastic valve seats 48, 50, 52, 54 machined directly or connect to housing 12 by suitable means, such as a resilient snap lock mechanism including an annular end 49 having a radial flange 49a retained against a step 51 on the inside of housing 12. Each of valve seats 48, 50, 52, 54 carry conventional tilting disc cardiac valves 48a, 50a, 52a, 54a disposed directly therein for permitting uni-directional flow only, as will be explained hereafter. Each of valve seats 48, 50 in inlet ports 38, 40 have screwthreads that receive an external collar 56. Collar 56 retains an outer flange 57 of a cuff ring (graft insert) 58a, to which an atrial cuff graft 60a is secured by an external resilient plastic snap ring 62. The associated openings of bladders 14 and 16 are folded over tubular, beaded end portions 59 of seats 48, 52 and 50, 54, respectively, and held in place by ring 58a or 58b.

Figure 8:
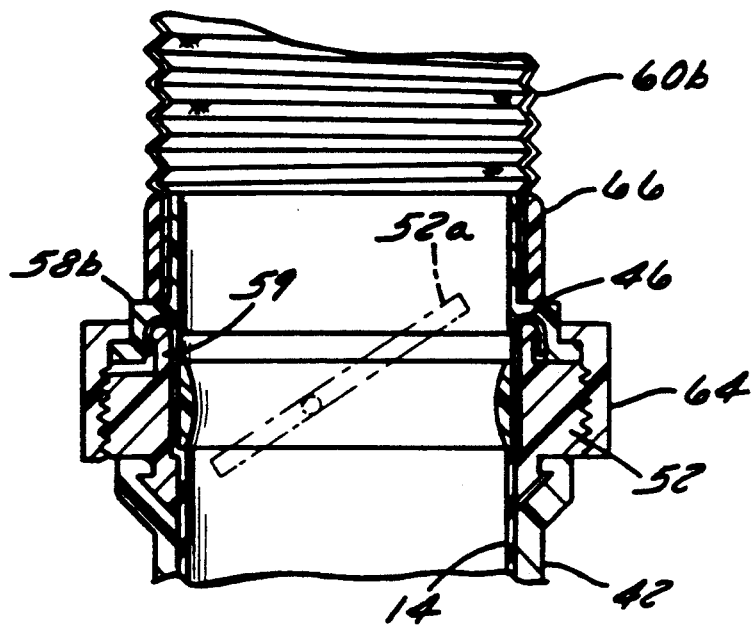
FIG. 8 is an enlarged detail view of the outlet valve seats shown in FIGS. 2-4.

In similar fashion, referring to FIG. 8, each of valve seats 52, 54 in outlet ports 42, 44 screw-threadedly receive a collar 64 which is rotatably disposed over flanged cuff ring 58a to which an aortic/pulmonic graft 60b is fixed by a snap ring 66. Atrial cuff and aortic/pulmonic grafts 60a, 60b, preferably made of dacron, are sutured to the host atrial and aortic/pulmonic arteries in order to provide blood flow channels between the host and bladders 14, 16. The aforementioned structures integrate the valves with housing 12, simultaneously retain bladders 14, 16 in position, and facilitate quick connection of bladders 14, 16 with the host arteries and veins. The plastic parts described in connection with the valve assemblies are preferably made of an acetal polymer plastic (Delrin).

Returning to FIG. 1, pusher plate assembly 18 is disposed between bladders 14, 16. Plate assembly 18 includes two circular plastic pusher plates 72, 74 connected together in spaced parallel relationship by a central plastic rod 76. Each of pusher plates 72, 74 has an disc-shaped outer surface 72a or 74a having a rounded edge substantially spanning and in engagement with a surface of bladder 14 or 16, respectively, so that back-and-forth motion of pusher plate assembly 18 alternatively compresses bladders 14, 16 to fill and pump blood therefrom.

The inner surfaces of bladders 14, 16 may be lined with a protective layer of living endothelial cells in order to help prevent blood clots from forming within the artificial heart. One procedure is given in Rupnick et al., *J. Vasc. Surg*, 1989 Vol. 9, pages 788-795, the contents of which are incorporated by reference herein. In addition, the flaccid, rounded nature of bladders 14, 16 provides a smooth surface on which clots are less apt to form than accordion-style bladders having sharp corners.

Mechanical linkage 20 cooperates with motor 22 to provide reciprocal, cyclic movement of pusher plate assembly 18. Linkage 20 comprises a lever arm 78, carriage 80, a connecting link 82, a crank arm 84 and a pair of guide rollers 86. Lever arm 78 has a first or distal end 88, a second or proximal end 90 and is mounted to pivot on a central pin 92 intermediate first and second ends 88, 90. Pin 92 is rigidly secured to or integrally formed with an inner projection 98 of housing 12. Pin 92 is mounted at or near the middle of lever arm 78.

First end 88 of lever arm 78 is inserted in a central slot 94 through rod 76 and connected by a pin 96 for pivotal movement with respect to rod 76. Second end 90 of lever arm 78 projects into in an aperture 100 formed in carriage 80. Second end 90 has a cylindrical roller 91 mounted on a transverse axle 93. The outer periphery of roller 91 is confined for rolling contact with the inner walls of aperture 100.

Rollers 86 project laterally from the one side of carriage 80. Rollers 86 are confined and move reciprocally in a guide track 102 (FIG. 4) formed on the inside of housing 12. A stepped end 104 of connecting link 82 is pivotally mounted by a pin 106 in a bifurcated end 108 of carriage 80, while the other end 110 of connecting link 82 is pivotally mounted by a pin 112 to the outer end 114 of crank arm 84. One end of pin 112 is threadedly secured to outer end 114 or arm 84. Crank arm 84 is, in turn, fixed for rotary movement in unison with a rotary drive shaft 115 of a gear reducer 118.

A high speed, unidirectional, three phase, brushless DC motor 22 operatively connected to reducer 118 operates drive shaft 115. Motor 22 generally operates at 3,000 to 6,000 rpm, and may have wires 116 for connection with an external motor drive circuit, or may be powered by induction using induction coils placed in the abdomen. One preferred system for powering an artificial heart according to the invention is the Ottawa TETS (transcutaneous energy transmission system) available from the Ottawa Heart Institute. The shaft bearings of motor 22 are its only moving parts, and have extremely long useful life. Motor 22 generally turns 50 times per full cycle of artificial heart 10. Gear reducer 118 is preferably a 50:1 reducer, such as manufactured by HD Systems of Wakefield, Massachusetts under the trademark Harmonic Drive. Reducer 115 is coupled to motor 22 to reduce speed and increase output torque of drive shaft 115.

Figures 9, 10:
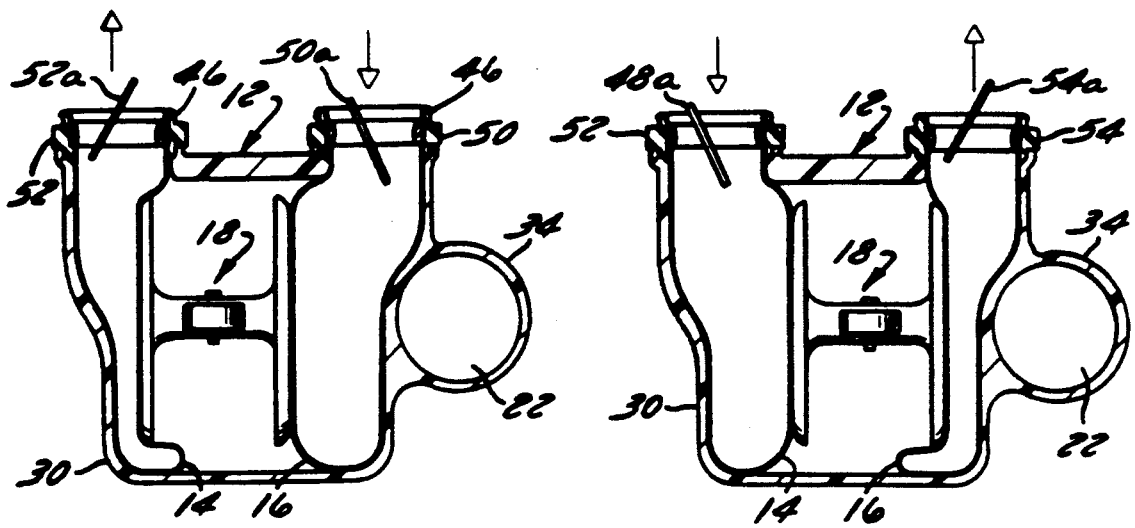
FIG. 9 and 10 are schematic diagrams of a cyclic operation of the artificial heart of FIG. 1.
Figure 7:
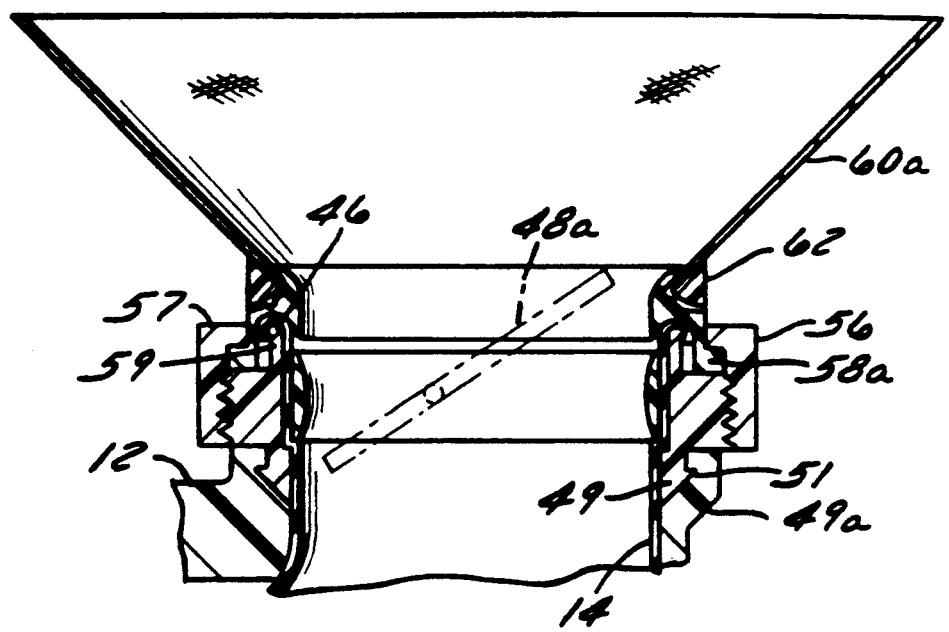
FIG. 7 is an enlarged detail view of the inlet valve seats shown in FIGS. 2-4.

Rotary drive force from motor 22 and rotating crank arm 84 will cycle connecting link 82 and associated carriage 80 along guide track 102, thereby pivoting lever arm 78 about pin 92 and causing reciprocal movement of pusher plate assembly 18 so that bladders 14, 16 alternatively fill with and eject blood when artificial heart 10 is implanted in a host. FIGS. 9 and 10 show the endmost positions of plate assembly 18. The drive force includes a component acting along a direction $F_1$, substantially parallel to and spaced from the longitudinal centerline P of rod 76. The drive force also includes another component $F_2$, acting along a longitudinal axis L of lever arm 78 and ultimately acting on one of bladders 14, 16 during compression thereof.

In operation, artificial heart 10 is passively filled through either of inlet valves 48a, 50a by the fill pressure of the implant host. Pusher plate assembly 18 alternatively forces blood out of each bladder 14, 16 via associated outlet valve 52a, 54a. Valves 48a, 50a, 52a, 54a act in concert to permit flow in one direction only to assure the bladders 14, 16 alternately intake and exhaust blood. For example, if bladder 14 is being compressed as shown in FIGS. 2 and 9 to eject blood, inlet valve 48a is closed while outlet valve 52a is open. Bladder 16, which is being filled with blood, has inlet valve 50a open and outlet valve 54a closed until the pusher plate assembly 18 shifts to the opposite configuration as illustrated in FIG. 10.

Figure 11:
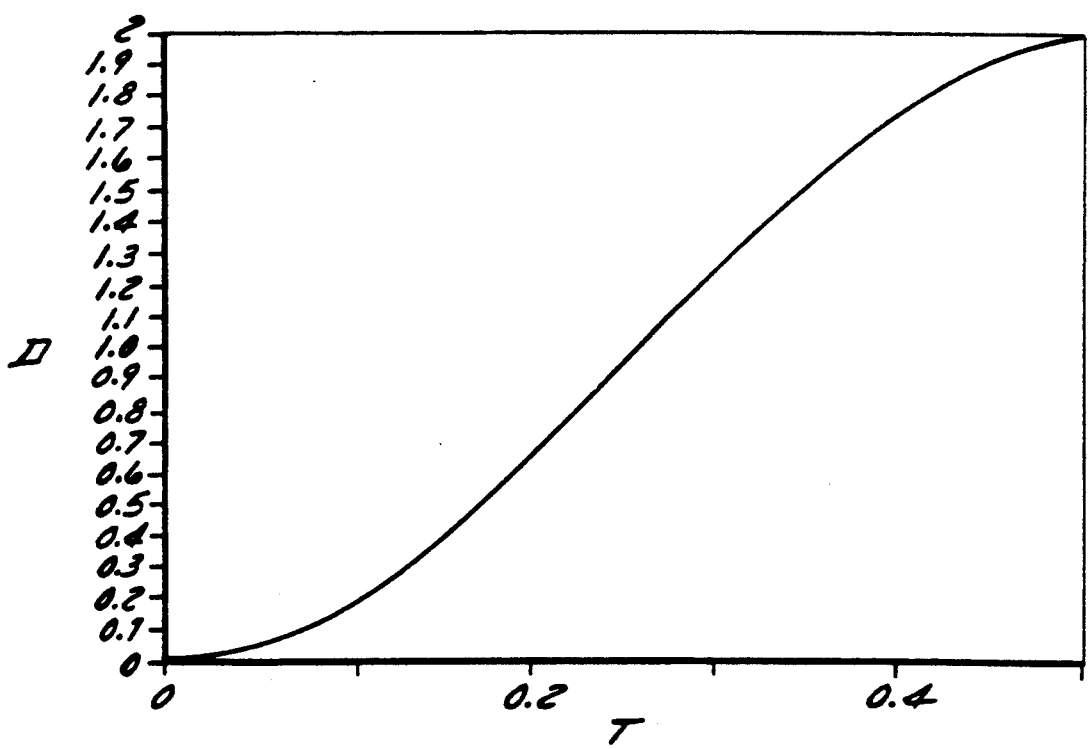
FIG. 11 is a graph depicting pusher plate displacement D in cm vs. time T in seconds for the artificial heart shown in FIG. 1 at 60 beats per minute during the compression phase.

In contrast to prior art devices, mechanical linkage 20 produces a pusher plate motion that is gentle to the blood. Variations in forces $F_1$ and $F_2$ due to the circular path of pin 112 cause compression of each bladder 14, 16 to begin at a slow pace, accelerate to a maximum and then decelerate to zero as the plate assembly stops and reverses its direction. The displacement of pusher plate assembly 18 follows a well behaved sinusoidal curve with respect to time as illustrated in FIG. 11. The blood within the artificial heart is thereby put into motion gradually before being accelerated to maximum velocity, and decelerated gradually before the pumping action stops.

Figure 12:
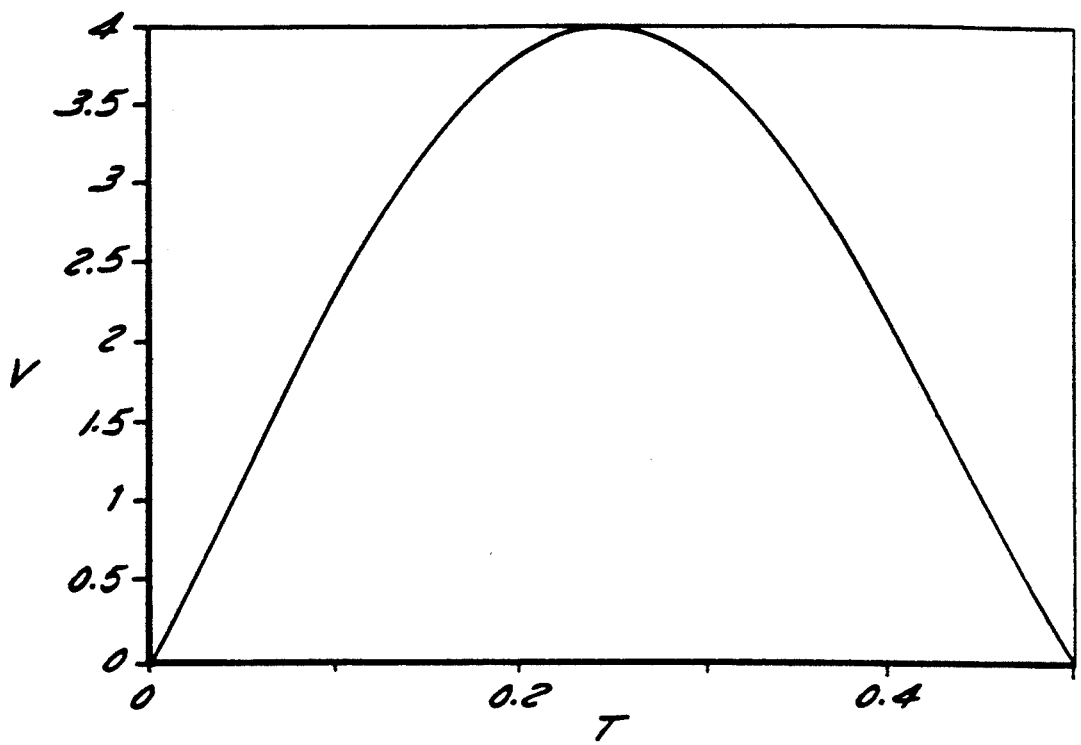
FIG. 12 is a graph depicting pusher plate velocity V in cm/sec vs. time T in seconds for the artificial heart shown in FIG. 1 at 60 beats per minute during the compression phase.

This ramp up/ramp down velocity curve, as shown in FIG. 12, gently closes inlet valves 48a, 50a and opens outlet valves 52a, 54a before the blood is placed under maximum compression. In particular, the velocity of the pusher plate assembly movement ranges from about 0 to a maximum that varies depending on heart rate, for example, 4 cm/sec at 60 beats per minute, as the plate assembly moves from zero to maximum speed and back to zero again. The ejection time of one ventricle may be different from the ejection time of the other in order to obtain the correct right-left balance of blood flow. These mechanical actions lessen valve trauma (hemolysis) to blood components and regurgitation of blood back through the inlet valve 48a, 50a, and also minimize the time derivative of pressure (dP/dt) to which the blood components are subjected.

Artificial heart 10 provides a variety of advantages over known artificial heart designs. As previously described, bladders 14, 16 are designed without crevices or corners where blood can accumulate and form undesirable thrombi or clotting. The large surface area of each pusher plate 72, 74 extending substantially across each bladder 14, 16 facilitates an efficient exhaust of blood from outlet ports 42, 44. Inlet ports 38, 40 distribute flow along the inner surfaces of bladders 14, 16. The inlet flow dynamics produce good mixing of the inflow blood, and a positive wash of the bladder walls so that stagnant circumferential areas are minimized. The exhaust flow dynamics direct the flow of blood to eliminate stress to the bladder lining, substantially reduce stagnant central areas, and gently force the outlet valves open early in the compression cycle. Further, location of the motor and reducer to the side of the bladders, rather than between them, reduces the overall size of the unit, permitting the artificial heart to fit better within the chest cavity and allowing the valve ports to be closer together, permitting better alignment to the associated natural anatomical structures.

Figure 13:
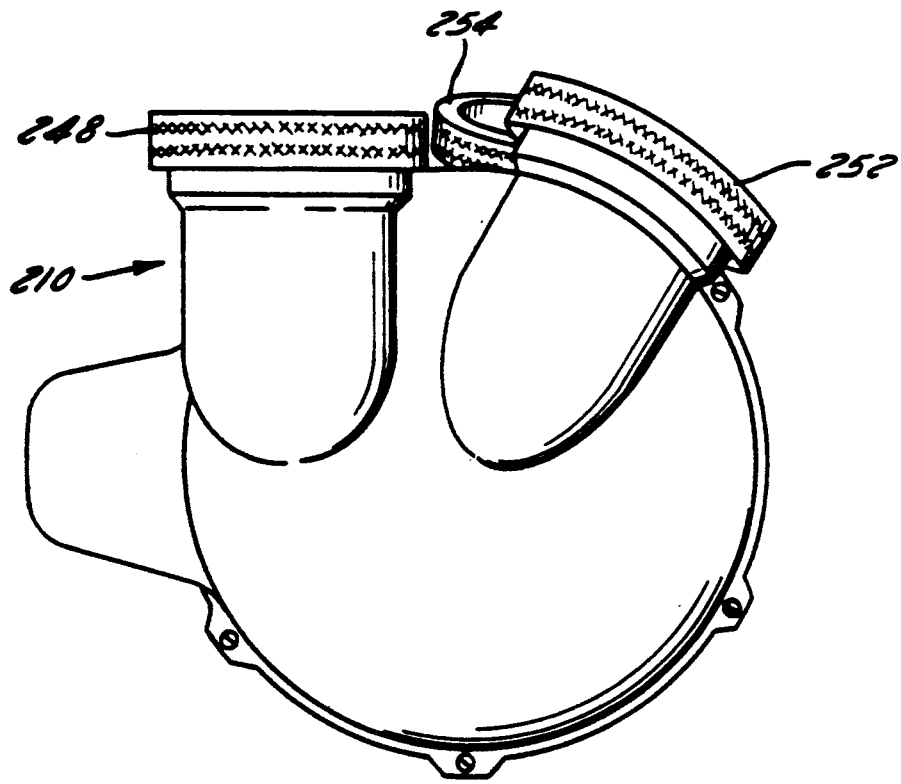
FIG. 13 is an end view comparable to FIG. 4 of an alternative embodiment of an artificial heart according to the invention, with grafts removed.
Figure 14:
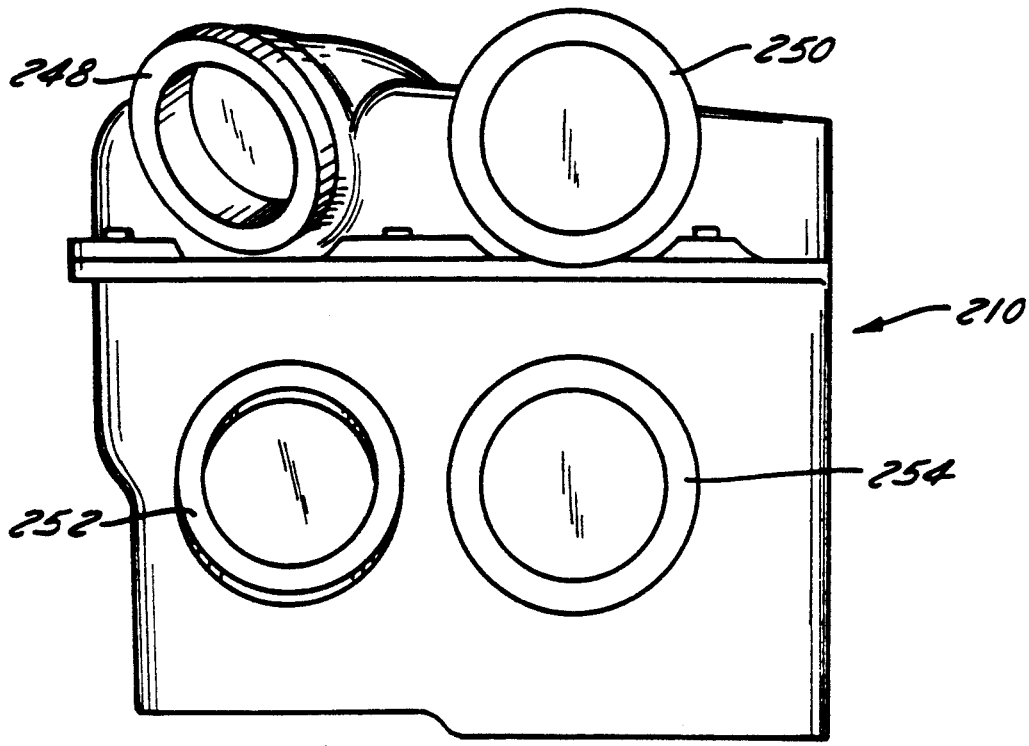
FIG. 14 is an elevational view of the housing of the artificial heart of FIG. 13.
Figure 15:
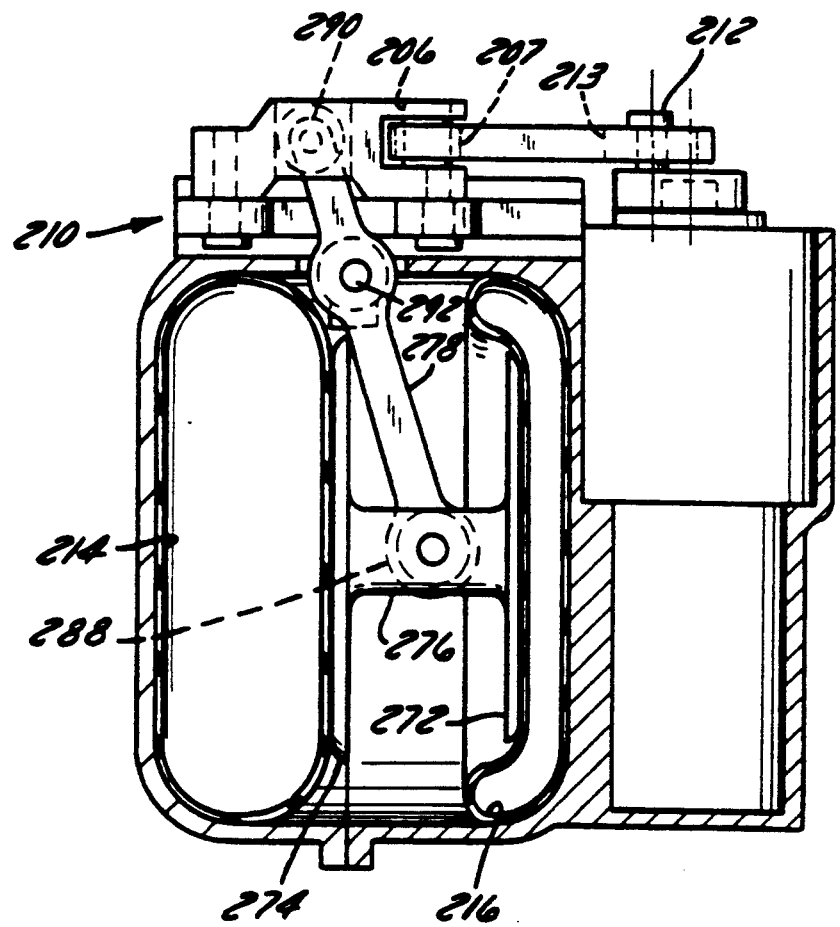
FIG. 15 is a lengthwise sectional view of the artificial heart according to FIG. 13.

FIGS. 13 to 15 show a modified form of artificial heart 210 according to the invention. Heart 210 differs from artificial heart 10 in several respects. In heart 210, pusher plate 272 on the right side of the heart is slightly smaller than the plate 274 on the left side to allow for the physiological need for less blood on the right than on the left. For example, plate 272 has a diameter at least 1 mm smaller than plate 274, preferably at least 5 mm smaller than plate 274. Pivot pin 292 is located closer to the second end 290 of lever arm 278 in order to shorten connecting rod 276 and thereby allow bladders 214, 216 to be disposed closer together. Pin 292 may, for example be positioned about one-third of the length of the length of arm 278 from its second end 290 and about two-thirds of the length of arm 278 from first end 288.

Pin 292 is preferably disposed sufficiently high so that one or both of the pusher plates move to a position directly beneath pin 292 at the end of a cycle, as shown in FIG. 15. The resulting decrease in spacing of bladders 214, 216 moves inlet valve seats 248, 250 and outlet valve seats 252, 254 even closer together, making it easier to mount heart 210 to the natural anatomical structures remaining after removal of the natural heart. In either embodiment according to the invention, pivot pins 206, 212 are preferably mounted in respective ball bearings 207, 213 to facilitate smooth operation.

The invention thus provides a cyclic action, dual pusher plate, electromechanically-operated artificial heart for alternately compressing a bladder containing blood directed to the pulmonary (right side) system and a bladder containing blood directed to the systemic (left side) circulatory system. The unit may be compact, i.e. measuring 105 mm×109 mm×95 mm. Due to the relatively simple mechanical design and the use of brushless DC motor, the artificial heart of the invention is highly reliable and consistently responds to the proper blood flow demanded by the host. The unit is extremely durable yet light in weight due to its simplicity of design and the small size of the actuator.

The sinusoidal displacement curve occurs as a result of the cam arm design. The latter provides for gradual acceleration and deceleration of the blood at the extremes of the piston stroke. The speed of the stroke will be varied depending on body blood demand, and the speed is preferably different for the right and left ejection phases. The motor may pause briefly at the end of each ejection phase, such as for about 25-50 milliseconds, to limit one bladder to filling during that time and to regulate right and left flow balance.

It will be understood that the above description is of the preferred exemplary invention and, the invention is not limited to the specific form shown. For example, the artificial heart 10 could include a device to vary the speed of motor 22 to regulate hear rate. Further, the means for varying the speed of compression and decompression of the chambers (bladders) could comprise electronics for varying the speed of the drive system, or other mechanical components capable of producing a velocity vs. time curve similar to FIG. 12. These and other modifications may be made in the described invention without departing from the scope thereof as expressed in the appended claims.

I claim:

1. A biocompatible, implantable artificial heart, comprising:
   a housing having first and second inlet ports and first and second outlet ports;
   first and second flaccid bladders disposed in the housing, the first bladder communicating with the first inlet and outlet ports and the second bladder communicating with the second inlet and outlet ports;
   pairs of one-way, inlet and outlet valves disposed in each inlet and outlet port, respectively, the inlet valves in the inlet ports permitting blood to flow into but not out of the bladders, and the outlet valves in the outlet ports permitting blood to flow out of but not into the bladders;
   a pusher plate assembly positioned between and contacting the bladders for alternately compressing one bladder while decompressing the other bladder by back-and-forth motion of the pusher plate assembly;
   a motor having a rotary drive shaft, which motor is mounted in the housing at a position offset from the pusher plate assembly, such that the motor is located at a position other than between the bladders; and
   a mechanical linkage connecting the motor to the pusher plate assembly, the mechanical linkage transmitting drive force from the motor to the pusher plate assembly to reciprocate the pusher plate assembly so that the first and second bladders alternately fill with and eject blood through the respective inlet ports and outlet ports when the artificial heart is implanted in a host.

2. The artificial heart of claim 1, wherein the pusher plate assembly comprises first and second spaced, parallel plates, each of the plates having an outer surface substantially spanning and in contact with a respective one of the first and second bladders, and a rod connecting the first and second plates.

3. The artificial heart of claim 2, wherein the mechanical linkage further comprises a lever arm, a first pivot connecting a first end of the lever arm to the rod of the pusher plate assembly, a second pivot mounting a mid-portion of the lever arm on the housing, and a connecting mechanism for moving a second end of the lever arm back and forth in response to actuation of the motor, causing the first end of the lever arm to move the pusher plate assembly back and forth as the lever arm moves about the second pivot.

4. The artificial heart of claim 3, wherein the connecting mechanism comprises a crank arm connected to the drive shaft, a connecting link attached to a distal end portion of the crank arm so that a first end of the link moves in a circular path with the crank arm, a reciprocating carriage for transmitting movement of the connecting link to the second end of the lever arm, and a third pivot connecting a second end of the connecting link to the carriage.

5. The artificial heart of claim 4, wherein the housing has a linear guide track formed on an interior surface thereof, and the carriage has a guide mounted thereon confined in the guide track for reciprocal movement therein.

6. The artificial heart of claim 5, wherein the guide comprises a pair of spaced rollers.

7. The artificial heart of claim 2, wherein the outer surface of the plate that contacts the bladder corresponding to the right side of a human heart has a smaller surface area than the outer surface of the plate that contacts the bladder corresponding to the left side of a human heart.

8. The artificial heart of claim 7, wherein the pusher plates are generally round, and the plate that contacts the bladder corresponding to the right side of a human heart has a diameter at least about 1 mm smaller than the plate that contacts the bladder corresponding to the left side of a human heart.

9. The artificial heart of claim 1, further comprising a gear reducer connecting the motor to the drive shaft.

10. The artificial heart of claim 1, wherein each of the bladders has a pair of tubular projections extending therefrom, which projections end in openings, and the valves include valve seats sealingly engaged with respective ends of the tubular projections of the bladders.

11. The artificial heart of claim 10, wherein each of the first and second outlet ports further includes means for attaching a first graft having a first end adapted for connection to an artery of the host and a second end in communication with the one-way outlet valve disposed in each of the outlet ports, and each of the first and second inlet ports further includes means for attaching a second graft having a first end adapted for connection to a vein of the host and a second end in communication with the one-way inlet valve disposed in each of the inlet ports.

12. The artificial heart of claim 11, wherein the means for attaching the first graft comprises a tubular graft insert, a first resilient snap ring securing the second end of the first graft to an outside surface of the graft insert, a collar retaining an end of the graft insert to the valve seat of the outlet valve, and means for securing the collar to the valve seat of the outlet valve.

13. The artificial heart of claim 12, wherein the means for securing the collar to the valve seat comprises mating threads formed on an inner periphery of the collar and an outer periphery of the valve seat.

14. The artificial heart of claim 12, wherein the means for attaching the second graft comprises a cuff ring, a second snap ring encircling the cuff ring, the second end of the second graft being retained between the cuff ring and the second snap ring, and a second collar disposed on the cuff ring for engagement with the valve seat of the inlet valve.

15. The artificial heart of claim 10, wherein said bladders are generally cylindrical and have rounded inner surfaces.

16. The artificial heart of claim 1, wherein the second bladder is located directly between the first bladder and the motor.

17. A biocompatible, implantable artificial heart, comprising:
- a housing having first and second inlet ports and first and second outlet ports;
- first and second flaccid bladders disposed in the housing, the first bladder communicating with the first inlet and outlet ports and the second bladder communicating with the second inlet and outlet ports;
- a pusher plate assembly positioned between the bladders including a pair of spaced pusher plates in continuous contact with each bladder, respectively, for alternately compressing and decompressing each bladder by back-and-forth motion of the pusher plate assembly;
- a pair of one-way inlet valves disposed directly within the first and second inlet ports, respectively, the inlet valves permitting blood to flow into but not out of the bladders;
- a pair of one-way outlet valves disposed directly within the first and second outlet ports, respectively, the outlet valves permitting blood to flow out of but not into the bladders;
- a drive system having a rotary drive shaft and a motor mounted in the housing to one side of the first and second bladders at a position offset from the pusher plate assembly, such that the motor is located at a position other than between the bladders, and the second bladder is located between the first bladder and the motor; and
- a mechanical linkage connecting the motor to the pusher plate assembly, the mechanical linkage transmitting unidirectional drive force from the motor to the pusher plate assembly to reciprocate the pusher plate assembly so that the first and second bladders alternately fill with and eject blood when the artificial heart is implanted in a host, said linkage including means for gradually varying speed of movement of the pusher plate assembly from a minimum that occurs when each bladder reaches maximum compression to a maximum that occurs approximately midway between associated minima.

18. The artificial heart of claim 17, wherein the drive system is operated to provide for pusher plate assembly movement at a rate which varies as a sinusoidal curve as the plate assembly moves from minimum to maximum speed and back to minimum speed again.

19. The artificial heart of claim 18, wherein the means for varying the speed of movement of the pusher plate assembly comprises a crank arm attached at a first end to a connecting link and at a second end to the drive shaft, so that a force acting on the pusher plate assembly varies as a function of a position of a distal end of the crank arm on a circular path.

20. The artificial heart of claim 17, wherein each of the first and second inlet ports and the first and second outlet ports include a dacron graft enabling communication from a blood supply of the host to the first and second bladders.

21. The artificial heart of claim 17, wherein the drive system is operated to provide for pusher plate assembly movement.

22. A biocompatible, implantable artificial heart, comprising:
- a housing having first and second inlet ports and first and second outlet ports,
- first and second compressible flaccid bladders having rounded inner surfaces and each having a pair of tubular extensions configured for connection one each of the inlet and outlet ports, which bladders define first and second chambers in the housing, the first chamber communicating with the first inlet and outlet ports and the second chamber communicating with the second inlet and outlet ports,
- a pair of one-way inlet valves disposed directly within the first and second inlet ports, respectively, the inlet valves permitting blood to flow into but not out of the bladders,
- a pair of one-way outlet valves disposed directly within the first and second outlet ports, respectively, the outlet valves permitting blood to flow out of but not into the bladders, and
- a drive system for alternately compressing the chambers to fill and eject blood in a manner that resembles a natural heart, wherein the improvement comprises a system that varies speed of compression and decompression of the chambers from a minimum that occurs when each bladder reaches maximum compression to a maximum that occurs approximately midway between associated minima at a rate which varies as a sinusoidal curve as the speed of compression and decompression of each chamber moves from minimum to maximum speed and back to minimum speed again.

* * * * *